US006489589B1

(12) United States Patent
Alexander

(10) Patent No.: US 6,489,589 B1
(45) Date of Patent: *Dec. 3, 2002

(54) FEMTOSECOND LASER UTILIZATION METHODS AND APPARATUS AND METHOD FOR PRODUCING NANOPARTICLES

(75) Inventor: Dennis R. Alexander, Lincoln, NE (US)

(73) Assignee: Board of Regents, University of Nebraska-Lincoln, Lincoln, NE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/035,231

(22) Filed: Mar. 5, 1998

Related U.S. Application Data

(62) Division of application No. 08/193,371, filed on Feb. 7, 1994, now abandoned.

(51) Int. Cl.[7] .......................... B23K 26/38; B23K 26/40
(52) U.S. Cl. ................................. 219/121.69
(58) Field of Search .................. 219/121.7, 121.71, 219/121.72, 121.67, 121.68, 121.69, 121.61, 121.62, 121.6, 121.85; 606/11, 10, 12

(56) References Cited

U.S. PATENT DOCUMENTS 3,549,733 A * 12/1970 Caddell ................. 219/121.85

(List continued on next page.)

FOREIGN PATENT DOCUMENTS

WO 89/08529 * 9/1989

OTHER PUBLICATIONS

Translation of WO 89/08529, Jun. 1997.*

"Micromachining of Diamond Substrates with Waveguide Excimer Lasers", by Christensen, pp. 14–21 of *Lasers as Tools for Manufacturing* in the Proceedings of SPIE—The International Society for Optical Engineering, Sep. 1993.*

Excimer–Laser Etching of Diamond and Hard Carbon Films by Direct Writing an Optical Projection, J. Vac. Sci. Technology B4(1), Jan./Feb. 1986 by Rothschild et al.*

"Nanosecond and Femtosecond Excimer Laser Ablation of Fused Silica", by Ihlemann et al., pp. 363–368, *Applied Physics* A 54, Dec. 1992.*

*Primary Examiner*—Geoffrey S. Evans
(74) *Attorney, Agent, or Firm*—Suiter & Associates PC; Scott C. Rand; William J. Breen, III

(57) ABSTRACT

The present invention teaches various femtosecond machining and drilling apparatus and processes for fabricating tools and the like from both traditional and non-traditional materials. Also described are novel tools such as scalpels, and nozzles fabricated from the apparatus and processes of the present invention. Likewise, the present invention may be utilized in both a novel propulsion system and the production of materials formed from nanometer sized particles and the like.

12 Claims, 8 Drawing Sheets

U.S. PATENT DOCUMENTS

| | | | |
|---|---|---|---|
| 4,289,952 A | 9/1981 | Haggerty | 219/121.6 |
| 4,752,668 A | 6/1988 | Rosenfield et al. | 219/121.82 |
| 4,835,361 A | 5/1989 | Strom | 219/121.68 |
| 4,973,160 A | 11/1990 | Takiguchi et al. | 356/346 |
| 5,033,853 A | 7/1991 | Frangineas, Jr. | 356/346 |
| 5,093,549 A * | 3/1992 | Iwai et al. | 219/121.67 |
| 5,103,841 A | 4/1992 | Okumoto et al. | 219/121.77 |
| 5,243,589 A | 9/1993 | Stuke et al. | 369/100 |
| 5,248,877 A * | 9/1993 | Cooper et al. | 219/121.72 |
| 5,265,109 A | 11/1993 | Knox | 372/18 |
| 5,280,491 A | 1/1994 | Lai | 372/24 |
| 5,290,992 A | 3/1994 | Lin et al. | 219/121.68 |
| 5,324,281 A * | 6/1994 | Muller | 219/121.6 |
| 5,329,090 A | 7/1994 | Woelki et al. | 219/121.68 |
| 5,349,155 A | 9/1994 | Yamagishi et al. | 219/121.71 |
| 5,377,043 A | 12/1994 | Pelouch et al. | 359/326 |
| 5,383,198 A | 1/1995 | Pelouch et al. | 372/18 |
| 5,396,362 A | 3/1995 | Yakymyshyn | 359/245 |
| 5,410,125 A * | 4/1995 | Winston et al. | 219/121.71 |
| 5,432,151 A * | 7/1995 | Russo et al. | 427/596 |
| 5,461,234 A | 10/1995 | Miyazaki et al. | 250/372 |
| 5,489,984 A | 2/1996 | Hariharan et al. | 356/360 |
| 5,541,947 A | 7/1996 | Mourou et al. | 372/75 |
| 5,585,020 A | 12/1996 | Becker et al. | 219/121.85 |
| 5,656,186 A | 8/1997 | Mourou et al. | 219/121.69 |
| 5,720,894 A | 2/1998 | Neev et al. | 216/65 |
| 5,730,924 A | 3/1998 | Katoh et al. | 264/488 |
| 5,757,839 A | 5/1998 | Biswal et al. | 372/72 |
| 5,761,111 A * | 6/1998 | Glezer | 365/106 |
| 5,786,560 A * | 7/1998 | Tatah et al. | 219/121.85 |
| 5,984,916 A * | 11/1999 | Lai | 606/11 |
| RE37,585 E * | 3/2002 | Mourou et al. | 219/121.69 |

* cited by examiner

FEMTOSECOND LASER UTILIZATION METHODS AND APPARATUS AND METHOD FOR PRODUCING NANOPARTICLES

CROSS REFERENCES

The present application is a divisional of U.S. application Ser. No. 08/193,371 filed Feb. 7, 1994 now abandoned.

GOVERNMENT RIGHTS

The present invention was privately funded. The government has no rights in the present invention.

TECHNICAL FIELD

The present invention is generally related to methods for machining material and more particularly to a method and apparatus for machining nontraditional materials such as diamond, ceramics, and the like.

BACKGROUND ART

Known to the art are various apparatus and methods for machining materials. Such apparatus include those commonly utilized in manufacturing traditional materials (i.e., metals and the like). However, such manufacturing apparatus are poorly suited for machining nontraditional materials (i.e., diamond, ceramics and the like).

Advancements in the material sciences has produced a myriad of new materials. Many of these materials are hard and brittle and therefore difficult or impossible to successfully to drill or shape with standard machinery equipment. Lasers have been utilized with some limited success in cutting and drilling some of these new materials. However, the continuous or long pulsed lasers (nanosecond or longer) couple ineffectively with the surface of the material and a great portion of the laser energy goes into heating the plasma which produce large thermal gradients in the processed material which adversely affect the materials properties near the laser interaction region. Additionally, the long pulsed lasers known to the machining art are limited to several hundred pulses per second. These fundamental limitations, in the machining art, limit the potential use for a wide array of important new materials.

Femtosecond pulse generating lasers are known to the art. Lasers of this type are capable of generating pulse lengths presently as short as 5 femtoseconds ($5 \times 10^{-15}$ seconds) with pulse frequencies presently as high as 10 KHz. Various methods for utilizing such lasers are also known and described in the art. For example, a method of producing electrical pulses having an extremely narrow pulse width is described by Rauscher, et al. (U.S. Pat. No. 4,870,295); a method of detecting atomic and molecular motion is described by McClelland, et al. (U.S. Pat. No. 5,151,594); a femtosecond ultraviolet laser utilizing ultra-thin beta barium is described by Edelstein, et al. (U.S. Pat. No. 5,034,951); a broadly tunable high repetition rate femtosecond optical parametric oscillator is described by Edelstein, et al. (U.S. Pat. No. 5,017,806); a real time method of processing picosecond and femtosecond laser pulses is described by Cutolo, et al. (U.S. Pat. No. 5,007,717); a method of obtaining ultra fast spectral data utilizing a femtosecond laser is described by Heilweil, et al. (U.S. Pat. No. 4,980,566); and a method of investigating surfaces at nanometer and picosecond resolution is described by Beha, et al. (U.S. Pat. No. 4,918,309). Additionally, Elsayed-Ali, et al. describes a femtosecond time-resolved thermomodulation of thin gold films having different crystal structures (*Physical Review* 47:13 599–13 610); and Reitze, et al. has measured the optical properties of liquid carbon utilizing a femtosecond spectrometer (*Physical Review* 45:2677–2693).

DISCLOSURE OF INVENTION

The present invention teaches various femtosecond machining and drilling apparatus and processes for fabricating tools and bulk materials and the like from both traditional and non-traditional materials. Also described are novel tools such as scalpels, and nozzles fabricated from the apparatus and processes according to the present invention. Likewise, the present invention may be utilized in a novel propulsion system, the production of new and unique materials formed from nanometer sized particles, and in surgical and dental procedures, for example, in the preparation of a tooth for a filling, and the like.

MODES FOR CARRYING OUT THE INVENTION

I. Introduction

Figure 1:
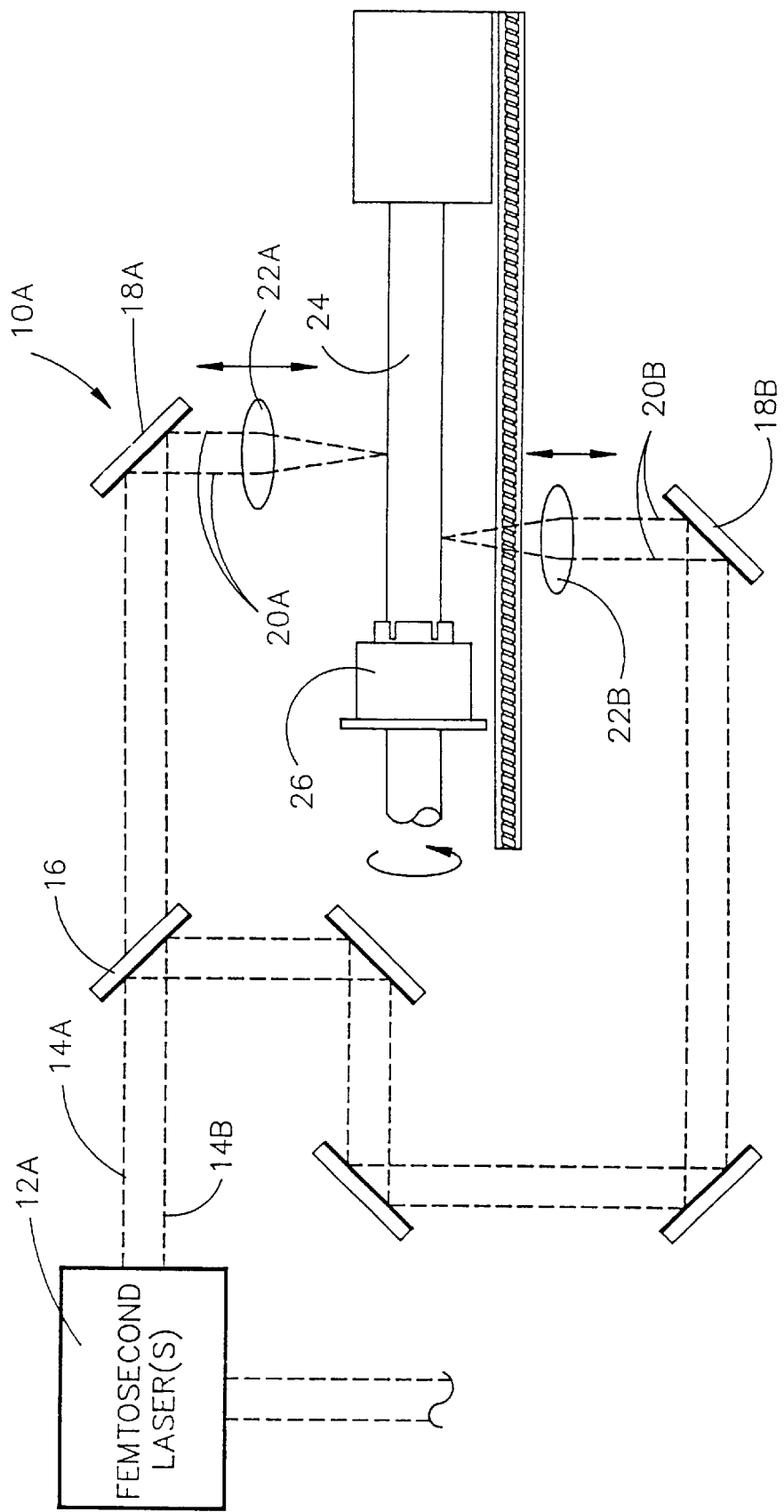
FIG. 1 is a diagrammatic illustration of a preferred embodiment of a femtosecond laser machining apparatus which may be utilized to perform the various machining processes of the instant invention.
Figure 2:
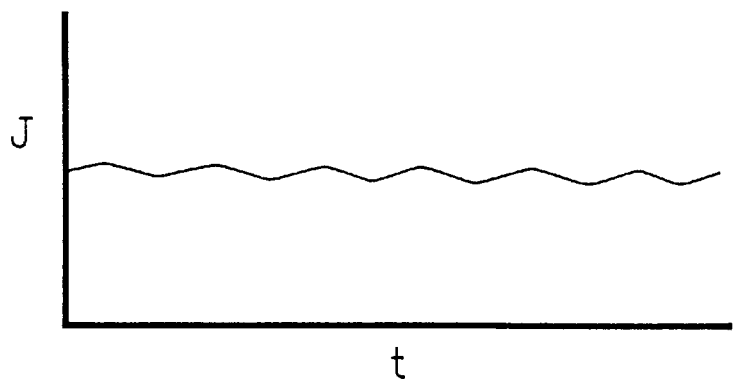
FIG. 2 is a graphical representation illustrating the output over time of a prior art and conventional carbon dioxide laser apparatus.
Figure 3:
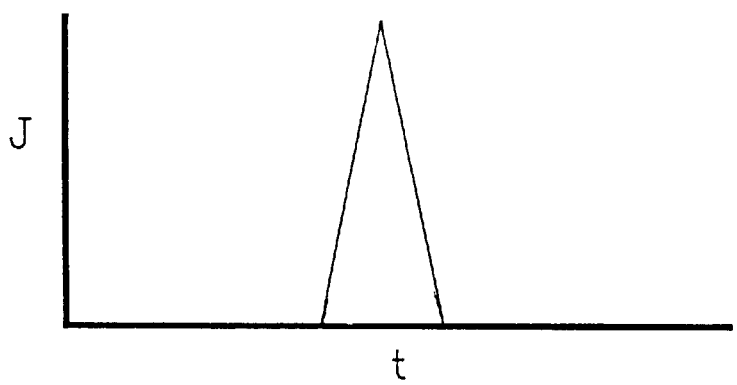
FIG. 3 is a graphical representation illustrating the output over time of a prior art nanosecond laser apparatus.
Figure 4:
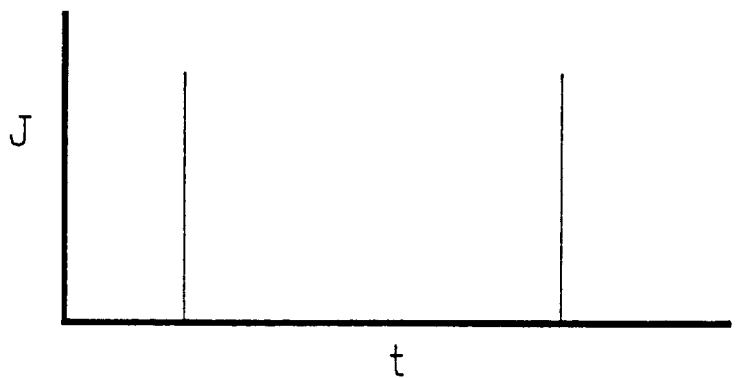
FIG. 4 is a graphical representation illustrating the output over time of an exemplary embodiment of a femtosecond laser apparatus of the present invention.

The following background is provided for those skilled in the art of conventional machining and related arts but unfamiliar with the operation of lasers.

A. Background

Laser light is produced when energy is used to excite certain atoms or molecules into specific energy patterns in an optical cavity with gain. Such light has the following characteristics: (1) coherence (both spatial and temporal); (2) directionality; (3) monochromaticity; and (4) brightness.

By encircling a synthetic ruby rod (having silvered mirrors directly evaporated on its ends) with a powerful quartz flashlamp, Theodore Maiman, produced a pulse of laser light on May 15, 1960. On Dec. 13, 1960 a group of physicist at Bell Laboratories produced the first continuous laser.

In 1704 Sir Isaac Newton [1642–1727] published a treatise on optics. In this work Newton proposed that light consisted of a stream of particles emitted from a light source that stimulated the sense of sight. Newton's theory met with general acceptance since it could successfully explained the laws of reflection and refraction. During this same period a Dutch physicist by the name of Christian Huygens [1629–1695] proposed a wave theory of light that also successfully explained the laws of reflection and refraction. Newton's particle theory was generally accepted over the wave theory proposed by Huygens until 1801. In that year Thomas Young [1773–1829] showed that light exhibited an interference behavior like that observed in waves.

Since it was impossible at the time to explain how particles could cause interference the wave theory gained acceptance over the particle theory. In 1873 James Clark Maxwell [1831–1879] proposed that light was a form of high energy electromagnetic waves, and united optical theory with the theories of electricity and magnetism. Maxwell predicted that these waves would travel at $3.00 \times 10^8$ m/s, and showed how his theory could explain both reflection and refraction.

However, Maxwell's electromagnetic theory could not explain what was known as the photoelectric effect. This effect was first observed by Heinrich Rudolph Hertz [1857–1894]. Hertz found that electrons were ejected from the surface of metal exposed to light, and that the kinetic energy of these electrons was independent of the intensity of the light. This directly contradicted the wave theory since it predicted that the energy produced by a beam of light would be proportional to the intensity of the beam of light.

In 1900 Max Planck [1858–1947] proposed that the energy of light waves were quantized in bundles of energy called photons. Using Planck's ideas Albert Einstein [1879–1955] was able to explain the photoelectric effect in 1905. Einstein suggested that the energy of a photon was proportional to the frequency of its electromagnetic wave:

$$E=hf,$$

where h is Planck's constant ($h=6.63 \times 10^{-34}$ J·s), and f is the frequency of the electromagnetic wave. Einstein's theory explained the photoelectric effect by suggesting that photons from the light source were absorbed by the electrons within the metal, and that the energy imparted on an electron, by a photon, was equal to hf. Einstein explained that this now more energetic electron would be ejected from the metal where it could overcome the metal's work function ($\phi$), and that the emitted electron (dubbed a photoelectron) would have a maximum kinetic energy equal to:

$$KE_{max}=hf-\phi.$$

Einstein also showed that a linear relationship existed between the frequency of the photons and the kinetic energy of the photoelectrons. Light is now considered to have a dual nature since it acts like both a wave and a particle.

B. Atomic Spectra

An electric current passed through an evacuated cylinder, filled with a noble gas, was found to produce a light with a characteristic color for different gases. This light passed through a narrow slit and viewed with a spectroscope showed a series of discrete lines known as line spectrum. The wavelength of these lines was found to be characteristic of the gas in the cylinder.

Joseph Balmer [1825–1898] found that the wavelengths of the line spectra in hydrogen could be described by the following equation.

$$1/\lambda=R((1/2^2)(1/n^2)),$$

where R is a constant known as the Rydberg constant equal to $1.0973732 \times 10^7$ m$^{-1}$, and where n is an integer from 3 to infinity. It was also observed that elements absorbed light at specific wavelengths (absorption spectra), which correlated with the wavelengths a particular element was observed to emit line spectra.

C. Bohr's Theory of the Hydrogen Atom

Physicists wondered why certain elements only emitted and absorbed certain wavelengths of light. Niels Bohr [1885–1963] proposed a model of the hydrogen atom to explain this phenomena. Bohr's theory made the following assumptions:

(1) Electrons move in circular orbits about a positively charged nucleus;

(2) Most of the atomic mass is concentrated in the positively charged nucleus;

(3) Electrons can exist in very specific orbits (Planck's quantum hypothesis). The only orbits that can exist are those for which the angular momentum of the electron is an integral multiple of $=h/2\pi$, h is Planck's constant ($6.626 \times 10^{-34}$ J·s). Since the angular momentum is quantized, we find:

$$mvr=nh,$$

where n equals an integer.

(4) While an electron is in one of its allowed orbits it is stable and does not radiate energy (these orbits are called stationary states).

(5) As an electron moves from one stationary state to another the radiation frequency obeys the following condition:

$$hf=E_i-E_f,$$

where $E_i$ and $E_f$ are the energies of the initial and final stationary states. Thus, the energy change is equal to a photon.

After making these assumptions Bohr was able to calculate the allowed energies of the hydrogen atom from the wavelengths of the hydrogen spectral lines:

$$PE=k(q_1q_2/r)=k[(-e)(e)]/r=-k(e^2/r),$$

where k is Coulomb's constant ($9.0 \times 10^9$ N·m$^2$/C$^2$), and the total energy E of the atom is the sum of the kinetic and potential energy of the electron:

$$E=KE+PE=\tfrac{1}{2}mv^2-k(e^2/r).$$

If we apply Newton's second law to the electron we find that the force of attraction $ke^2/r^2$ on the electron must equal $ma_r$, where $$a_r=v^2/r.$$

Therefore, the kinetic energy of an electron is equal to:

$$\tfrac{1}{2}mv^2=ke^2/2r,$$

and the total energy of the atom E is equal to:

$$E=-(ke^2/2r).$$

From this we may find the velocity v of an electron:

$$v^2=(n^2\,^2/m^2r^2)=ke^2/mr,$$

and the radius r:

$$r_n=(n^2\,^2/mke^2),$$

where n is an integer.

The Bohr radius $(r_0)_f$ where n=1 is equal to 0.529 therefore:

$$r_n = n^2 r_0 = n^2(0.529).$$

With Bohr's theory we may also determine the energies of the quantum states:

$$E_n = -(mk^2 e^4/2^2)(1/n^2) = 13.6/n^2 eV.$$

Thus, the lowest energy state (ground state), where n=1, the energy level is −13.6 eV. Where n=2 the energy level is −3.4 eV.

The amount of energy necessary to completely remove the electron from the atom (n→∞), is called the ionization energy. The ionization energy for hydrogen is 13.6 eV.

Bohr's theory (from the fifth postulate) may be utilized to calculate the frequency f of the photon emitted as an electron moves to another stable state:

$$f = (E_i - E_f)/h = (mk^2 e^4/4\pi^3)(1/n^2_f - 1/n^2_i).$$

Since the velocity of light c is equal to:

$$c = \lambda f,$$

and the frequency f is:

$$f = (E_i - E_f)/h = (mk^2 e^4/4\pi^3)(1/n^2_f - 1/n^2_i),$$

the wavelength λ of each spectral series is equal to:

$$1/\lambda = f/c = mk^2 e^4/4\pi c^3 (1/n^2_f - 1/n^2_i).$$

Combining Balmer's series we find that:

$$R = mk^2 e^4/4\pi c^3.$$

Since R derived from Bohr's theory was in agreement with experimental data, Bohr's theory could be shown to successfully predict the wavelengths of the observed spectral lines of hydrogen. While Bohr's planetary model agreed with observed data for the hydrogen atom it could not describe the optical spectra for more complex atoms.

D. Bohr's Correspondence Principle

While Newtonian mechanics successfully describes quantum mechanics where the value of n<10,000, relativistic corrections are required for particles traveling with the velocities maintained by electrons. To find $m_f$ we may use the following equation:

$$m_f = m_i/[1-(v/c)^2].$$

Both energy and mass are related by Einstein's energy equation:

$$E = mc^2_f$$

thus, the potential energy PE is equal to:

$$PE = m_i c^2_f$$

and the kinetic energy is equal to:

$$KE = E - PE = mc^2 - m_i c^2 = m_i c^2(1/[1-(v/c)^2]-1).$$

II. Laser Physics

An atom will only emit or absorb radiation at frequencies corresponding to the energy separation between the atom's discrete energy levels. Lasers capitalize on three phenomena that occur when electromagnetic waves interact with a material. These three phenomena are spontaneous and stimulated emission, and the absorption process.

A. Stimulated Absorption

A photon (γ) incident on an atom, with energy hf matching the ΔE ($E_{f-Ei}$) between two energy levels of an atom, may be absorbed by that atom. This process is known as stimulated absorption.

If a cylinder containing a gas is illuminated with sun light, only those photons having frequencies corresponding to the energy difference between the atom's discrete energy levels (ΔE) will be absorbed. In this process a photon imparts its energy hf on a ground state electron, and that as a result of this added energy the electron moves to the next energy level.

B. Spontaneous Emission

An atom in an excited state, like that occurring after stimulated absorption, may return to a lower energy level by spontaneous emission. This process is the opposite of stimulated absorption. In this process a photon having hf=$E_2$−$E_1$ is ejected from an electron, and an electron moves from $E_2$ to $E_f$. The frequency of the ejected photon will be equal to:

$$f = (E_2 - E_1)/h.$$

In lieu of ejecting a photon, an atom may also move from one energy level to another by delivering some of its kinetic energy to surrounding atoms. Under normal circumstances an atom will remain in an excited state for only about $10^{-8}$ s.

C. Stimulated Emission

The photons produced during stimulated emission produce the intense, coherent light emitted by lasers. During this process an atom in an excited state interacts with a photon with a frequency equal to that of a spontaneously emitted photon. In this process there is a finite probability that such an interaction will cause an electron in $E_2$ to emit a photon as it moves to $E_1$. Note that in this process two in phase photons (the incident and emitted photon) will be ejected from the atom. Thus, by initiating stimulated emission in excited atoms intense coherent light is produced.

A laser has three essential components: (1) a lasing material consisting of either a gas, liquid, or solid; (2) a method of exciting this material (called pumping); and (3) a method of amplifying a signal applied to the lasing material (amplifier).

D. Basic Principles of Laser Action

The following three conditions must be achieved in order to produce laser action: (1) population inversion; (2) the lasing material must be in a metastable state; and (3) the emitted photons must cause further stimulated emissions in other atoms within the system (this step is usually created by reflection).

1. Population Inversion

Normally the atoms within a closed system are in a ground rather than an excited state. Therefore, where light is incident on the atoms in such a system more photons will undergo stimulated absorption than stimulated emission. Laser light cannot be produced under these conditions. In order to achieve laser action population inversion must occur. This simply means that the system must contain a greater number of atoms in an excited state than in a ground state. In other words, there must be fewer atoms willing to absorb photons than atoms willing to undergo stimulated emission. Once population inversion has been achieved a net emission of photons can be obtained.

2. Metastability

In order for laser action to occur the lasing material must be in a metastable state so that stimulated emission will occur prior to spontaneous emission. Such a state can only be created and maintained where there is a net flow of energy into the system.

3. Amplification

As photons are ejected during stimulated emission they are reflected back through the lasing material so that they will produce optical gain by stimulated emission within the system.

4. Laser Action

The three before mentioned conditions are realized by utilizing a multiple level scheme. Note that an incoming electromagnetic wave would produce far more transitions from $E_1 \to E_2$ than transitions from $E_2 \to E_1$. Because of this is impossible reaching and sustaining a population inversion in a two-level system. This is called two-level saturation.

In order to achieve laser action more than two energy levels must be utilized. By using multiple level laser schemes it is possible to maintain population inversion and a steady state optical gain.

E. Characteristics of Laser Light

Laser light has four characteristics: (1) directionality; (2) monochromaticity; (3) coherence (both spatial and temporal); and (4) brightness.

1. Directionality

The photons of a laser beam follow the same vector. This is a consequence of the resonant cavity containing the lasing material. Only electromagnetic waves propagating in this direction can be sustained within the cavity. Since only unidirectional waves may be propagated in the cavity the laser output consists of a single, highly collimated and directional beam.

2. Monochromaticity

Laser output is nearly a perfect monochromatic wave (usually represented as a sine wave) with a bandwidth of close to zero. This is caused by the two mirror arrangement on either side of the lasing system cavity. The oscillations can only occur at the resonant frequencies of the cavity.

3. Coherence

There are two types of coherence found in electromagnetic waves, spatial, and temporal.

a. Spatial Coherence

Imagine two points on the same wavefront at $t_0$. If both $P_1$ and $P_2$ lie in the same wavefront at $t_0$, the electromagnetic field at these two points will be in phase. Since it can also be said that both $P_3$ and $P_4$ will be in the same wavefront the corresponding electromagnetic field at these points will also be in phase. Therefore, such a wave is said to have spatial coherence.

b. Temporal Coherence

An electric field that undergoes phase changes at time intervals equal to $\alpha t$ is said to have temporal coherence. The bandwidth of a wave in temporal coherence is given by:

$$\alpha f 1/ t_0.$$

4. Brightness

Laser beams of just a few milliwatts have a brightness many orders of magnitude greater than that found in even the brightest conventional sources.

III. Femtosecond Laser Apparatus

A. Background

Ultrafast laser apparatus and their operation are known to the art, see for example, M. Murname and H. Kapteyn, The Recent Revolution in Femtosecond Lasers, IEEE LEOS Newsletter, August, 1993, p. 17; J. Glanz, Short-Pulse Lasers Deliver Terawatts on a Tabletop, R&D Magazine, April 1993, p. 54; and especially, H. Messenger, Technology of ultrafast fast lasers and electro-optics expands rapidly, Laser Focus World, September 1993, p. 69. The present invention claims processes and apparatuses for utilizing an ultrafast laser source and does not claim a particular ultrafast (femtosecond) laser source. However, a brief background in ultrafast laser sources may prove useful to those unskilled in the operation of such sources.

1. Ultrafast Pulse Manipulation

The product of the lower limit of laser pulse duration and spectral band-width cannot exceed one. Therefore, the temporal and spatial profiles of coherent laser pulses are Fourier transforms of each other. For this reason lasing materials with a broad gain bandwidth are necessary to produce ultrafast pulses. Suitable materials are at least one of certain organic dye solutions and tunable solid-state media such as Ti:Sapphire, Cr:LiSAF, and forsterite.

Additionally, since conventional optical materials cause dispersion (broadening of the pulse-width due to the refractive index which changes wavelength) as pulses gate through materials, shorter (bluer) wavelengths are delayed relative to longer (redder) wavelengths (positive dispersion) in a process known as "chirping." In order to compensate for linear chirping, pairs of gratings or prisms are utilized to produce negative dispersion to compensate for the positive dispersion produced by the optical materials. In this manner redder wavelengths are minimized such that the original pulse may be recovered.

Certain components may selectively filter or retard some frequency components of the pulse. For this reason conventional optical components must be carefully matched. Additionally, single-stack coatings are preferred over multilayer dielectric coatings since the different layers reflect some frequency components differently. This may alter the relative phases of certain frequency components such that the temporal profile of the pulse is destroyed.

Preferably non-linear optical components such as frequency-doubling and tripling crystals are utilized which are specifically designed for ultrashort pulses. Components of this type are available from CAS Co. (Culvert City, Calif.). For example, in order to frequency-double 100-fs or 10-fs pulses crystals must be 1 mm thick or less or thinner than 100 $\mu$m respectively.

Pulse duration may be determined through autocorrelation measurements. This may be accomplished by splitting a pulse via partial reflection in a 50:50 beam splitter, the two pulses are then crossed inside a second-harmonic-generation (SHG) crystal, and the SHG intensity is then measured as one pulse is variably delayed (SHG crystal thickness must be minimized to obtain accurate measurements).

2. Ultrafast Laser Pulse Production

Ultrafast pulses (in the femtosecond range) may be produced by modelocking conventional c.w. sources. This may be accomplished in active modelocking schemes by placing an acousto-optic mode-locker in the laser cavity. RF power is then applied so as to generate an acoustic standing wave in the modelocker thereby causing light to be defracted from the cavity. Whenever the standing wave is at or very near a null, lasing will occur for a brief period. However, the frequency v of the A-O modelocker must be matched to the cavity length L for stable operation since spacing between pulses T is given by 2L/c where c is the speed of light and v=2T.

In an exemplary embodiment modelocked c.w. solid-state lasers (with an applied RF of 50 MHz) are 90 ps from the 1064-nm line and 70 ps from the 532-nm line of Nd:YAG and 40 ps and 30 ps from the 1053- and 527-nm lines, respectively, of Nd:YLF.

In order to increase the pulse energy, Q switches are placed in the cavity to build up large inversions in the laser medium. Switching the q-switch off allows lasing to occur with far higher energies than in conventional c.w. modelocked operation. Cavity dumping may also be utilized in order to select single output pulses from Q-switched lasers. In such an embodiment an electro-optic Pockels cell rotates the pulse polarization and removes it from the pulses. These high-peak-pulse energies, which increase tens of microjoules into millijoules (from 150 $\mu$J to 1.2 mJ for the 1064-nm wavelength of Nd:YAG) are useful for ultrashort amplification schemes.

Excimer and copper-vapor lasers may also be utilized as pump sources for ultrafast dye lasers. Since copper-vapor lasers operate at very high repetition rates, amplification of colliding-pulse modelocked dye laser output is possible.

3. Ultrafast Pulse Manipulation

In order to achieve high pulse energies short pulses may be stretched or "chirped", then amplified, and then recompressed back to the original pulsewidth or, if desired, amplified again. Chirped pulse amplification was first demonstrated at the University of Rochester in Nd:glass. Since then, it has been applied to Ti:Sapphire, alexandrite, and Cr:LiSAF. Terawatt systems are becoming more common, and table-top terawatt lasers are currently under development.

Ultrafast laser sources are available from COHERENT, SPECTRA-PHYSICS, and CONTINUUM. Control electronics and amplifier systems are available from POSITIVE LIGHT and MEDOX RESEARCH.

4. Wavelength Tuning

Since the lasing materials utilized have broad gain bandwidths short pulse output is tunable. Systems such as Coherent's Mira 9000 and Spectra-Physics' Tsunami provide modelocked tunable output over the Ti:sapphire tuning range. Frequency doubling may also be utilized to extend output to visible wavelengths.

Other schemes have also been utilized to produce tunable ultrafast output in the infrared via difference-frequency mixing in nonlinear materials such as $LiNbO_3$ and KTP. Optical parametric oscillators have also been successfully utilized to generate tunable radiation.

B. Description of Exemplary Embodiments

The interaction of laser light with condensed matter (solid or liquid) has been extensively studied for both c.w. and nanosecond pulses (particularly in the area of nuclear fusion by inertial confinement (Hughes).

The high peak powers of femtosecond lasers are obtained via small amounts of energy delivered in several femtoseconds (1 to several hundred). In carrying out the invention the high peak powers are concentrated utilizing optical focusing components. For example, if a 50 mJ, 150 fs pulse is focused down to a 3 $\mu$m spot the intensity is about $10^{18}$ W/cm$^2$ at extreme outputs shielding should be utilized as x-rays may be produced). Material subjected to these electric field strengths are ionized by both linear and nonlinear processes. Material is removed without any significant heat transfer to the surrounding atoms since during these shorts pulse times atomic nuclei are nearly stationary. Because of the large mass of the atomic nuclei, high temperatures and pressure may be generated on a highly localized scale which is not possible with previous longer pulsed laser.

In exemplary modes for carrying out the invention, a low pulse rate may be sufficient to accomplish the desired result, however, in other applications 10–100 KHz pulse rates may be required. For example, kilo Hertz rates may be employed in machining applications where rapid material removal is desired (such as in boring or machining applications).

Femtosecond lasers are commercially available and one common example are dye lasers with compressed pulse means. The currently preferred system of the present invention utilizes a Ti:Sapphire based system. However, in carrying out the invention any femtosecond laser with energies greater than the desired material removal threshold are adequate.

Figure 11:
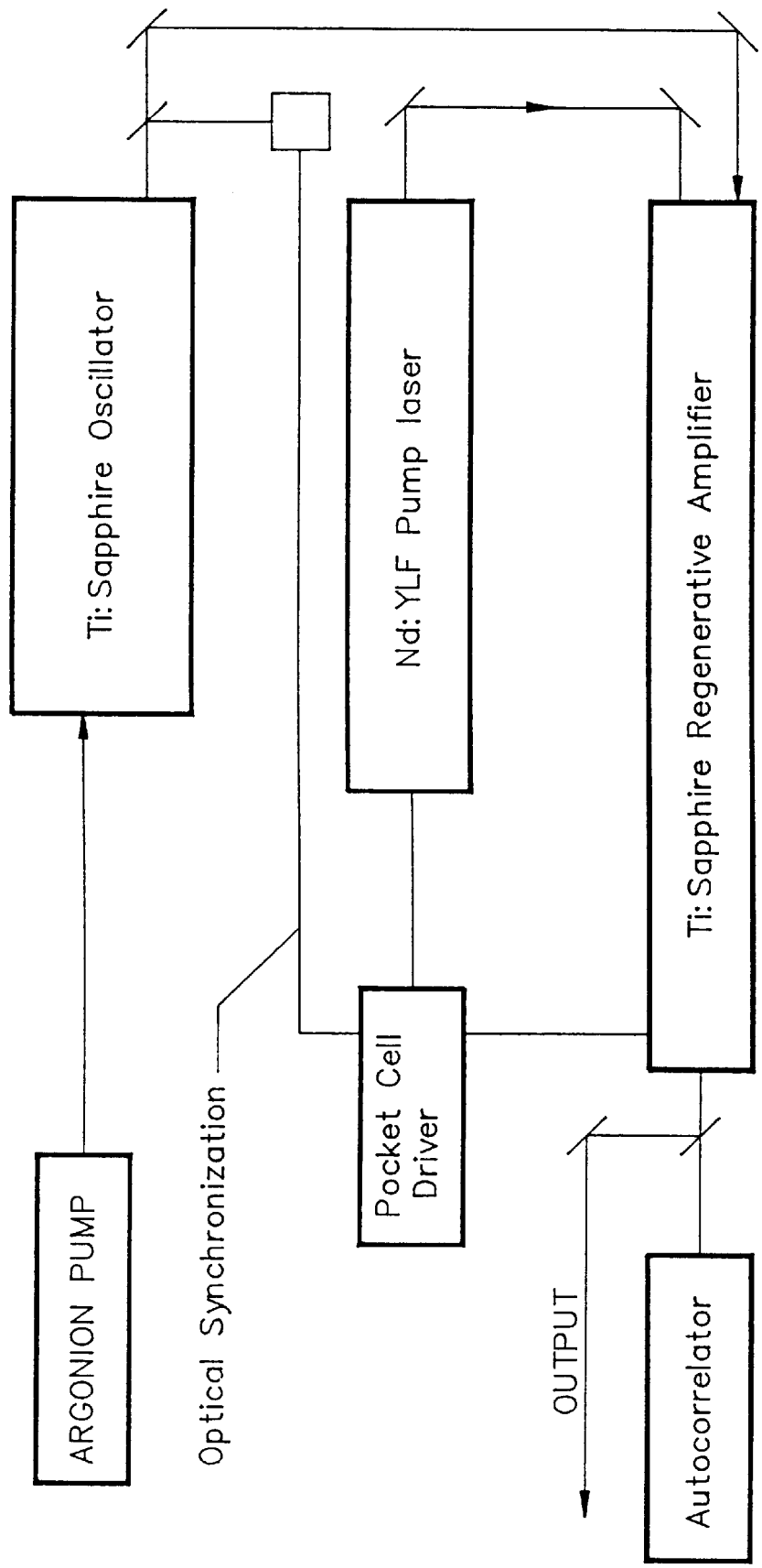
FIG. 11 is a diagrammatic view of a preferred femtosecond laser apparatus.

The preferred method is to optimize the material removal rate. The femtosecond laser wavelength affects skin penetration depth and the material removal rate (the skin depth is a function of both the complex optical properties of the material and the laser wavelength). A diagrammatic illustration of an exemplary ultrafast laser source is illustrated in FIG. 11.

C. Femtosecond Laser Machining

1. Materials

Femtosecond laser machining may be carried out on both conductive (metals) and non-conductive (insulators) materials. For example, stainless steel, gold, copper, iron, nickel, titanium, silicon, and diamond have all been machined according to the present invention utilizing an exemplary apparatus of the present invention (10–20 $\mu$J of 150 fs pulses).

2. Methods

The laser machining method of the present invention may be conducted in atmospheric conditions, an inert gas atmosphere, or in a vacuum. If machining is performed under atmospheric conditions surface oxidation is possible. Machining in an inert gas atmosphere or in a vacuum both reduce oxidation and surface plasma on the machined part.

Figure 8:
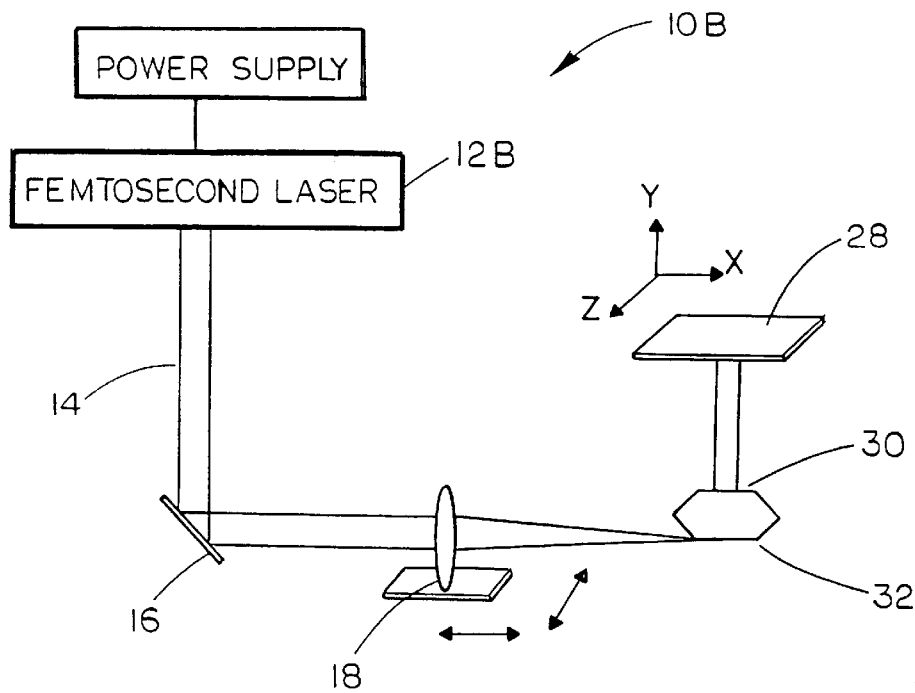
FIG. 8 is a diagrammatic illustration of a femtosecond laser tooling apparatus for fabricating diamond tools.

The part may be machined using a single laser beam or in a multi-beam or multi-laser configuration (FIGS. 1 and 8). Either the part may be moved or the laser beam may be oscillated to cover a wider area.

In a first preferred embodiment 10A a femtosecond laser 12A having one or more beams (14A, 14B) may be split via a beam splitter 16 such that the beam 14A is incident on a scanning mirror 18A and beam 14B is incident on a scanning mirror 18B. The resulting beams (20A, 20B) are then focused via adjustable/moveable focusing optics (22A, 22B) such that the beams are directed to a workpiece 24 held in a rotatably driven chuck 26. In this fashion (traditional horizontal lathe) parts may be machined in accordance with the present invention.

In a second preferred embodiment 10B a femtosecond laser 12B having one or more beams (14C, 14D) may be directed through focusing optics 22C such that the resulting beam may be directed at a diamond scalpel (or diamond(s) on a machine tool piece) 30 such that a very hard and finely honed edge 32 may be produced on the diamond scalpel (or diamond(s) on a machine tool) 30. The diamond scalpel (or diamond(s) on a machine tool) 30 may moved by a moveable platform 28 such that various portions of the workpiece (30) may be honed or machined.

3. Uses

The invention is particularly suited for machining standard metal surfaces as well as non-traditional hard and brittle materials (e.g. alumina, stainless steel, diamond, and silicon wafers). The invention is also useful in machining composite materials and the like.

D. Nanoparticles

Figure 9:
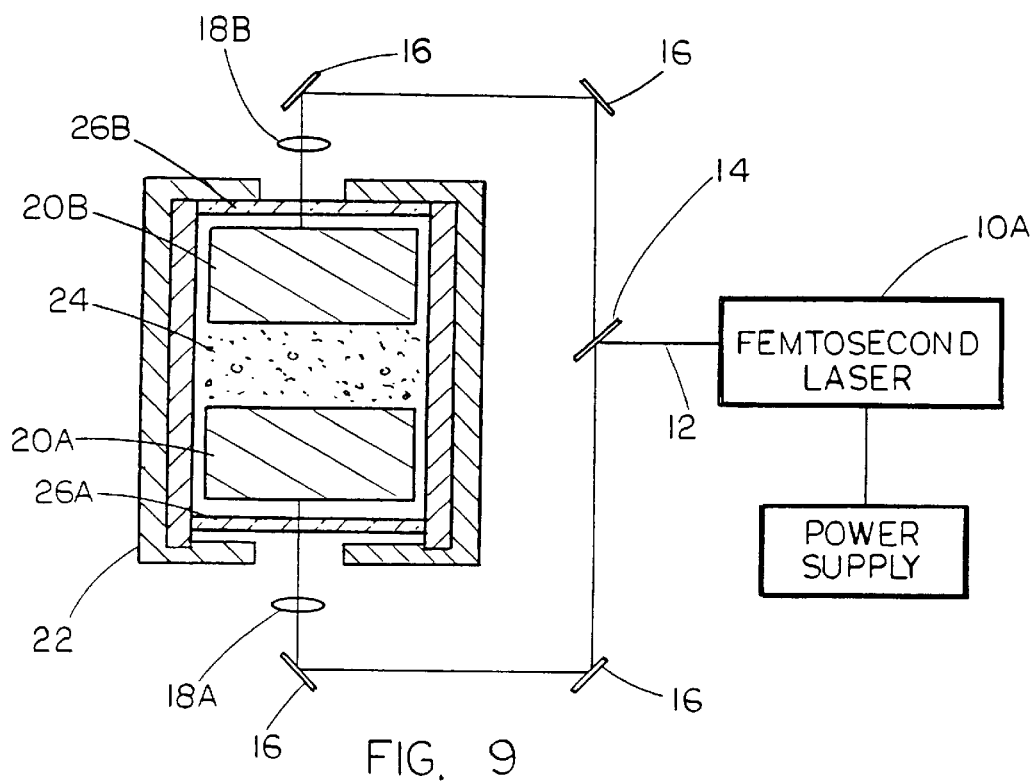
FIG. 9 is a cross-sectional diagrammatic view of an apparatus for agglomerating nanometer particles.

During the machining process of the present invention nanometer sized particles are formed as a result of the femtosecond laser beam interacting with the workpiece surface. The size of the nanometer particles produced depends on the power of the laser and the surrounding gas pressure. These nanostructures (FIG. 10) (nanoparticles) may be collected and reassembled to form new materials that have nanometer sized grain boundaries (FIG. 9). These materials, fabricated according to the present invention, have been shown to be up to ten times harder and stronger than the original material. Additionally, some of these materials have been shown to have different optical, mechanical, and electrical properties than bulk objects formed from the non-nanometer particle corresponding material.

Figure 10:
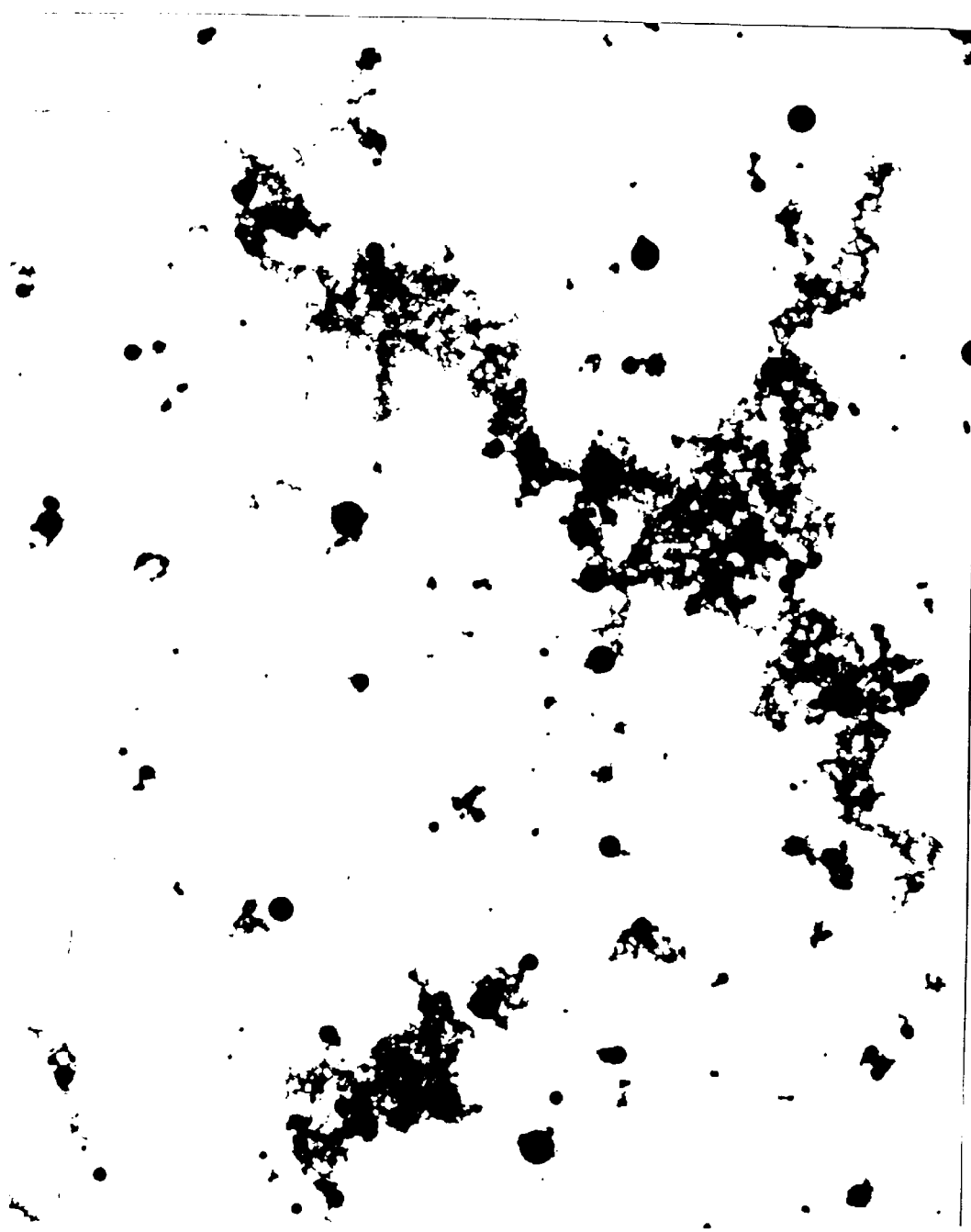
FIG. 10 is a micro-photograph of nanometer sized particles formed as a result of the machining process of the present invention.

Since the nanometer particles are collected there is no environmental waste and contamination and disposal problems are reduced. Likewise, the nanometer particles may also have a greater value than the original material from which they were generated. Additionally, the high frequency of the femtosecond laser makes it possible to rapidly machine and generate large quantities of small particles simultaneously (FIG. 10).

In a preferred and exemplary embodiment of the present invention nanometer particles (FIG. 10) may be agglomerated to form new materials. For example, as illustrated in FIG. 10, a femtosecond laser 10 may be utilized in such agglomeration process. The femtosecond laser pulses 12 may be directed so as to be incident on a beam splitter 14 so as to form the resultant femtosecond pulsed beams which may be directed by mirrors 16 and then focused via a pair of optical systems (18A, 18B) such that they strike a pair of opposing sliding laser acceleration blocks (20A, 20B) in a vacuum chamber 22 (equipped with windows 26A, 26B). It is also possible to fix one end of the accelerating blocks and only use one arm of the described agglomeration apparatus. Nanometer sized particles 24 are compacted and combined by the heat and force resulting from the force exerted on the particles 24 by the femtosecond laser driven opposing sliding laser acceleration blocks (20A, 20B). In this fashion new materials may be fabricated.

It should be apparent to those skilled in the art that other methods (e.g., explosives, or high pressure compaction techniques) of combining the nanometer particles may also be employed in accordance with the present invention. It is possible to simply sandwich the particles between 20A and 20B in the atmosphere or a desired gas environment.

E. Diamond High Pressure Nozzles

Figure 5:
FIG. 5 is a micro-photograph of a channel bored into a diamond utilizing an exemplary embodiment of the femtosecond laser machining apparatus of the present invention.
Figure 6:
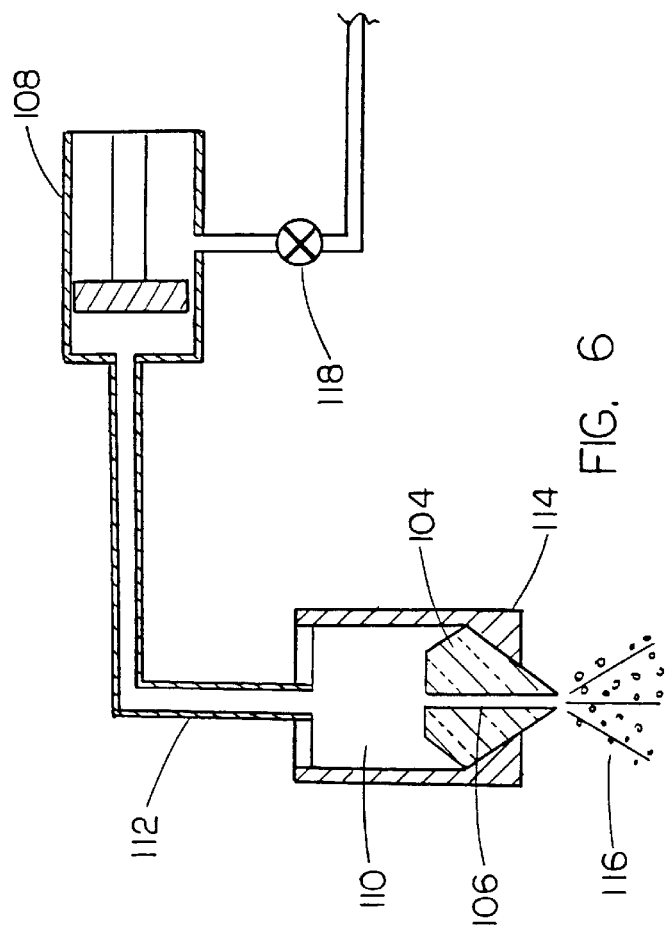
FIG. 6 is a cross-sectional diagrammatic view of a high pressure nozzle fabricated from the apparatus of the present invention.

The present invention may be utilized to produce high pressure nozzles (FIG. 6). A hole may be bored through a diamond (FIG. 5 illustrating a channel) such that the resulting workpiece may be utilized to form a nozzle for a liquid or slurry cutting apparatus (FIG. 6).

In a preferred embodiment of the present invention a diamond nozzle 102 may be fabricated from a diamond 104 having an aperture 106 bored therein by the femtosecond laser machining apparatus and process of the present invention (FIG. 1) so as to produce a liquid or slurry cutting apparatus 100 (FIG. 6). A high pressure pump 108 may be used to force a high pressure fluid or critical fluid or slurry mixture 110 through a line 112 into a nozzle support chamber 114 such that the high pressure fluid or critical fluid or slurry mixture 110 is forced through the aperture 106 in the diamond 104. In this fashion the resulting fluid column or spray 116 may be utilized for machining and the like (FIG. 6).

F. Femtosecond Laser Propulsion System

Figure 7:
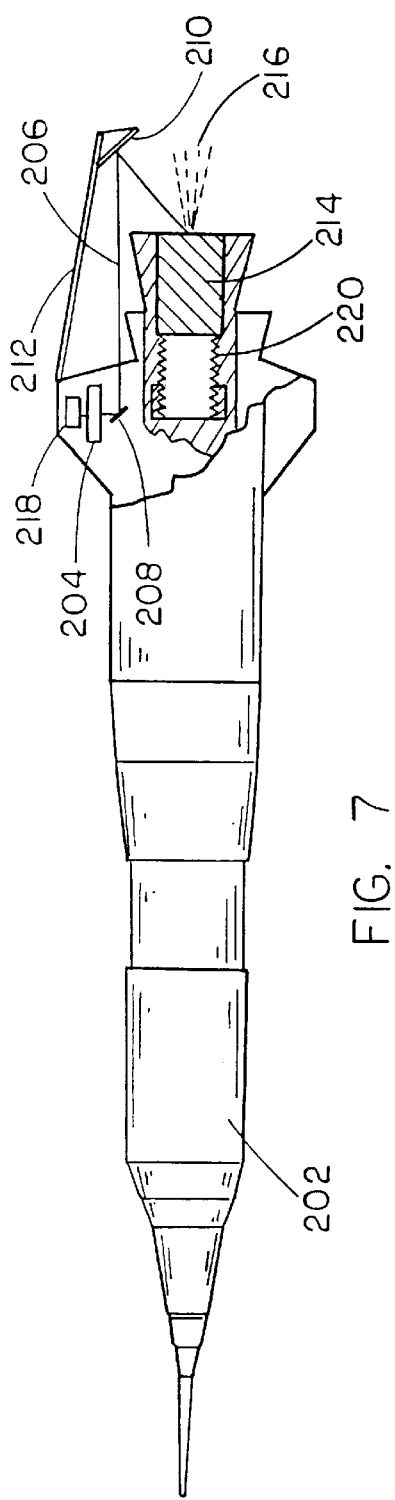
FIG. 7 is a diagrammatic illustration of a femtosecond laser propulsion system which utilizes the principles of the present invention.

The present invention may be adapted for use in a propulsion system (FIG. 7) wherein a femtosecond laser is utilized to accelerate fuel (ice or the like). In such an embodiment plasma and particles are accelerated from the material so as to propel the vehicle (F=ma). A propulsion system of this type might be utilized to propel spacecraft via photoelectric power cells or nuclear fuel powering the femtosecond laser (FIG. 7).

In a preferred embodiment of the present invention (FIG. 7) a femtosecond laser propulsion system 200 may be produced. A spacecraft 202 having a power supply 218 (photoelectric cells or nuclear power source or the like) and a femtosecond laser 204, for producing femtosecond laser pulses 206, and a mirror 208 for directing the pulses 206 to a beam steering mechanism 210 (supported by a beam steering mechanism support 212) such that the pulses are directed to a block of ice (or the like) 214 so as to cause material 216 to be propelled and ejected away from the spacecraft 202. In this manner the spacecraft 202 will be propelled by the material 216 ejected by the femtosecond laser 204. Additionally, a fuel extending mechanism 220 may be employed to project the fuel 214 to an optimum position (FIG. 7).

G. Medical Uses of Ultrafast Laser Pulses

Figure 12A:
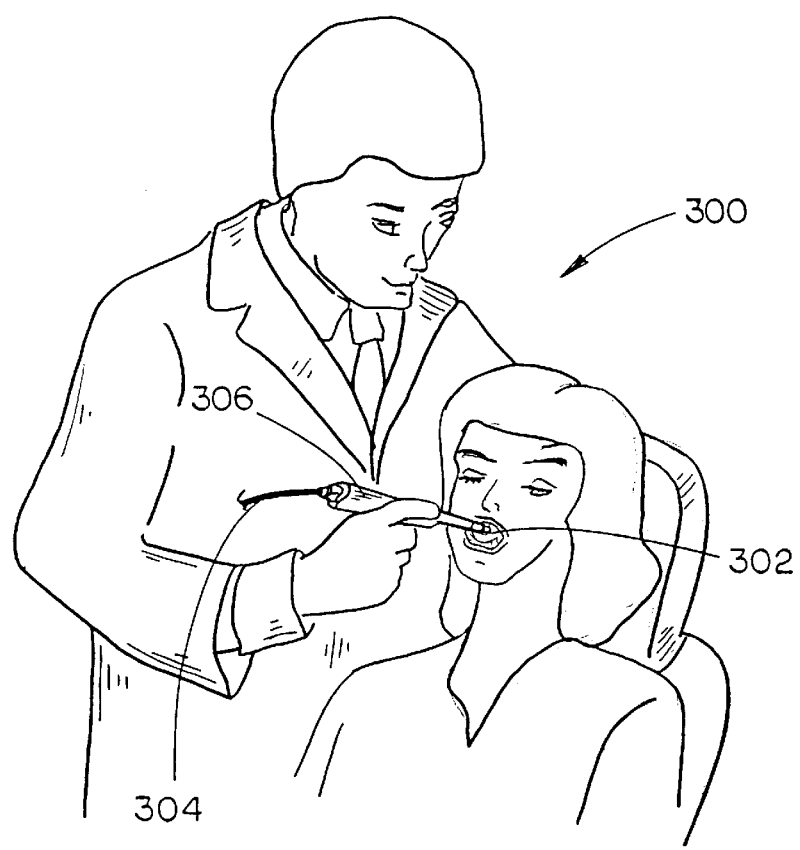
FIGS. 12A and 12B are perspective views showing embodiments of the present invention adapted for use in surgical procedures.
Figure 12B:
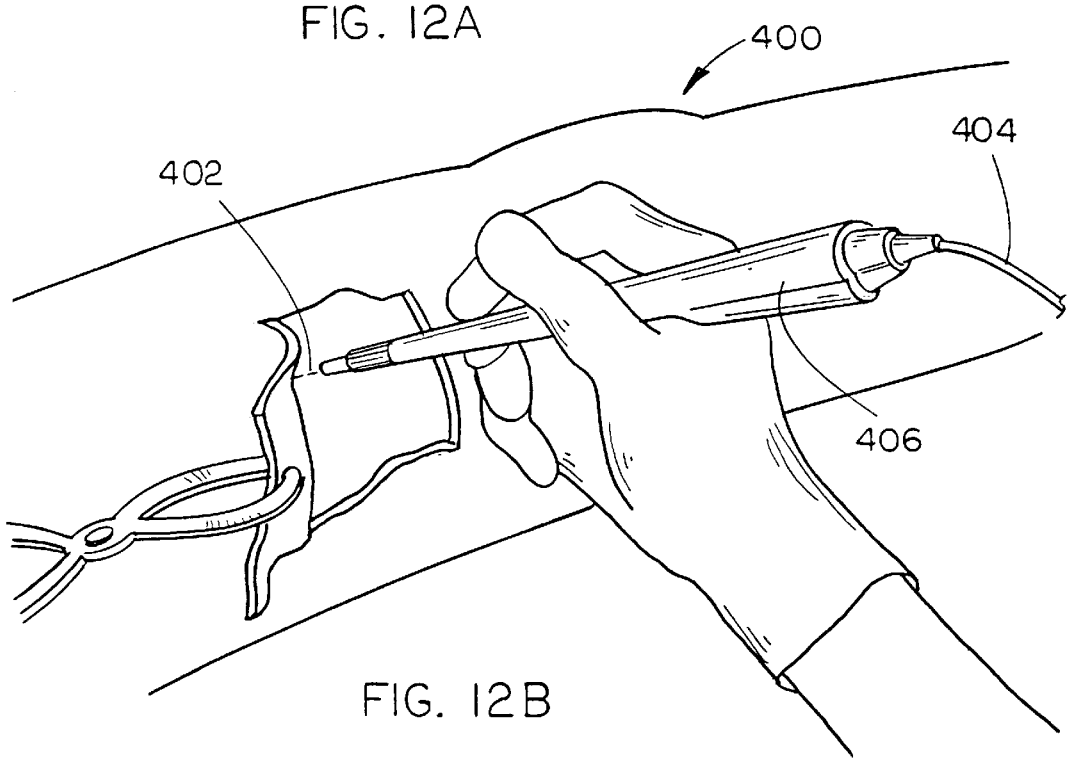

According to the present invention an ultrafast laser source (FIG. 11) may be utilized according to the present invention 300 (FIGS. 11 and 12A) and 400 (FIGS. 11 and 12B). In these embodiments of the present invention femtosecond laser beam pulses (302, 402) may be guided via a fiber-optic laser pulse guide (304, 404) to a hand-held unit (306, 406) adapted to activate condition and focus the emitted femto-second pulses for use in dentistry (FIG. 12A) surgery (FIG. 12B) [removal of burn tissue or the like from the surface or interior of the body] and the like.

What is claimed is:

1. A process for producing diamond nozzles, comprising boring an aperture through a diamond with femtosecond laser pulses, wherein said femtosecond laser pulses are generated at a rate less than the rate that would damage surrounding material.

2. The process of claim 1 wherein said femtosecond pulses have a pulse energy of at least 10 µJ.

3. The process of claim 2 wherein said femtosecond laser pulses are between 0.1 femtoseconds and 999 femtoseconds in length.

4. The process of claim 1 wherein said femtosecond laser pulses arc focused down to a spot size sufficient to produce material removal with both linear and non-linear processes.

5. A process for femtosecond laser machining, comprising:

directing femtosecond laser pulses at a part to be machined such that material may be selectively removed from said part to be machined, wherein said femtosecond laser pulses are focused down to a spot size sufficient to produce material removal with both linear and non-linear processes, wherein said femtosecond pulses are generated at a rate less than the rate that would damage surrounding material; and wherein the part comprises a metal.

6. The process of claim 5, wherein the part comprises a material selected from the group consisting of stainless steel, gold, copper, iron, nickel, and titanium.

7. The process of claim 5, herein the part comprises stainless steel.

8. The process of claim 5, wherein the part comprises titanium.

9. A process for femtosecond laser machining, comprising:

directing femtosecond laser pulses at a part to be machined such that material may be selectively removed from said part to be machined, wherein said femtosecond laser pulses are focused down to a spot size sufficient to produce material removal with both linear and non-linear processes, wherein said femtosecond pulses are generated at a rate less than the rate that would damage surrounding material, wherein the part comprises diamond.

10. A process for femtosecond laser machining, comprising:

directing femtosecond laser pulses at a part to be machined such that material may be selectively removed from said part to be machined, wherein said femtosecond laser pulses are focused down to a spot size sufficient to produce material removal with both linear and non-linear processes, wherein said femtosecond pulses are generated at a rate less than the rate that would damage surrounding material, wherein the part comprises ice.

11. A process for femtosecond laser machining, comprising:

directing femtosecond laser pulses at a part to be machined such that material may be selectively removed from said part to be machined, wherein said femtosecond laser pulses are focused down to a spot size sufficient to produce material removal with both linear and non-linear processes, wherein said femtosecond pulses are generated at a rate less than the rate that would damage surrounding material, and wherein the part comprises a material selected from the group consisting of diamond, silicon, alumina, ceramic materials, and ice wherein the femtosecond laser pulses are focused down to a spot size having an intensity on the order of $10^{18}$ watts per square centimeter.

12. A process for femtosecond laser machining, comprising:

directing femtosecond laser pulses at a part to be machined such that material may be selectively removed from said part to be machined, wherein said femtosecond laser pulses are focused down to a spot size sufficient to produce material removal with both linear and non-linear processes, wherein said femtosecond pulses are generated at a rate less than the rate that would damage surrounding material, wherein the femtosecond laser pulses are focused down to a spot size having an intensity on the order of $10^{18}$ watts per square centimeter.

* * * * *